(12) United States Patent
Chen et al.

(10) Patent No.: US 7,279,133 B2
(45) Date of Patent: Oct. 9, 2007

(54) PLANAR SENSOR AND A METHOD FOR MEASURING THE TEMPERATURE OF SAME

(75) Inventors: David K. Chen, Rochester Hills, MI (US); David P. Wallace, Davison, MI (US); Da Yu Wang, Troy, MI (US); Walter T. Symons, Grand Blanc, MI (US); Paul C. Kikuchi, Fenton, MI (US); Yingjie Lin, El Paso, TX (US); Lora Thrun, Grand Blanc, MI (US); Mark A. Shost, El Paso, TX (US); Joseph G. Ralph, Owosso, MI (US)

(73) Assignee: Delphi Technologies, Inc., Troy, MI (US)

( * ) Notice: Subject to any disclaimer, the term of this patent is extended or adjusted under 35 U.S.C. 154(b) by 763 days.

(21) Appl. No.: 10/029,049

(22) Filed: Dec. 20, 2001

(65) Prior Publication Data

US 2003/0119196 A1    Jun. 26, 2003

(51) Int. Cl.
*B32B 5/02* (2006.01)
*B32B 27/12* (2006.01)
*B32B 27/04* (2006.01)
*G01N 27/00* (2006.01)
*G01N 27/26* (2006.01)

(52) U.S. Cl. .................. 422/98; 422/82.01; 422/82.02; 422/82.04; 422/83; 436/136; 204/425; 204/426; 204/431

(58) Field of Classification Search ............. 422/82.01, 422/82.02, 82.04, 98, 83; 436/136; 204/425, 204/426, 431

See application file for complete search history.

(56) References Cited

U.S. PATENT DOCUMENTS 4,090,151 A    5/1978    Presset et al.

(Continued)

FOREIGN PATENT DOCUMENTS

JP    2001013105    12/2000

(Continued)

*Primary Examiner*—Brian Sines
(74) *Attorney, Agent, or Firm*—Paul L. Marshall

(57) ABSTRACT

In a planar oxygen sensor having a pump cell, a reference cell, a sensor chamber and a heating device, a ground plane electrode is provided and includes a sensing portion having a first sense lead and a second sense lead and a measuring portion having a first measuring lead and a second measuring lead, wherein the first measuring lead and the second measuring lead have increased surface area relative to said sensing portion such that the resistance between the first measuring lead and the second measuring lead is reduced and wherein the first measuring lead is disposed so as to be communicated with the first sense lead and the second measuring lead is disposed so as to be communicated with the second sense lead. Also, in a planar oxygen sensor having a pump cell, a reference cell, a sensor chamber, a heating device and a ground plane electrode that includes a sensing portion having a first sense lead and a second sense lead and a measuring portion having a first measuring lead and a second measuring lead, a method for measuring the temperature of the planar oxygen sensor is provided and includes obtaining a temperature measurement device, communicating the temperature measurement device with the first measuring lead and the second measuring lead, operating the planar oxygen sensor so as to cause the heating device to heat the planar oxygen sensor, and measuring the resistance between the first measuring lead and the second measuring lead.

4 Claims, 4 Drawing Sheets

U.S. PATENT DOCUMENTS

| | | | |
|---|---|---|---|
| 4,417,470 A * | 11/1983 | McCracken et al. | 374/136 |
| 4,719,441 A | 1/1988 | Horn | |
| 4,902,400 A | 2/1990 | Usami et al. | |
| 5,011,590 A | 4/1991 | Nakajima et al. | |
| 5,172,466 A | 12/1992 | Friese et al. | |
| 5,562,811 A | 10/1996 | Lenfers | |
| 5,989,398 A * | 11/1999 | Young et al. | 204/424 |
| 6,365,036 B1 * | 4/2002 | Polikarpus | 205/784.5 |
| 6,365,880 B1 | 4/2002 | Kikuchi et al. | |
| 6,401,521 B1 | 6/2002 | Nelson | |
| 6,435,005 B1 | 8/2002 | Kikuchi et al. | |
| 6,486,449 B2 | 11/2002 | Kikuchi et al. | |
| 6,562,215 B1 | 5/2003 | Nelson et al. | |
| 6,638,416 B2 * | 10/2003 | Wang et al. | 205/775 |

FOREIGN PATENT DOCUMENTS

| | | |
|---|---|---|
| JP | 200340403 | 1/2001 |

\* cited by examiner

PLANAR SENSOR AND A METHOD FOR MEASURING THE TEMPERATURE OF SAME

BACKGROUND

Planar oxygen sensors are used in a variety of applications that require qualitative and quantitative analysis of gases, such as applications that involve automobiles. In automotive applications, the relationship between the oxygen concentration in exhaust gases and the air-to-fuel ratio of a fuel mixture supplied to an engine allows the oxygen sensor to provide oxygen concentration measurements for determining optimum combustion conditions, maximization of fuel economy and efficient management of exhaust emissions.

Generally, a planar oxygen sensor consists of multi-layer ceramic structures and usually has a pump cell, a reference cell, a chamber between the pump cell and the reference cell, a heater and a ground plane electrode between the heater and the reference cell. The function of the oxygen sensor is to pump any residual oxygen from the chamber through the pump cell to the outside environment. As the oxygen ions, which are proportional to the oxygen concentration of the environmental gas being measured (in this case exhaust), flow through the pump cell an electric current proportional to the oxygen ion flow is generated thus allowing the oxygen concentration to be determined.

In many cases, in order to maintain an optimal level of precision and performance, the oxygen sensor should be operated at a fixed high temperature. Usually, to maintain the fixed temperature for best sensor function, temperature control is part of the sensor system with a temperature sensing feedback. As such, in chemical sensors constructed of electrolyte materials, such as zirconia, a typical temperature control incorporates the impedance measurement of the electrolyte material as the temperature feedback.

However, these designs have a number of drawbacks. First, the impedance of the electrolyte material can drift over the service life of the sensor and can affect the performance of the sensor or result in the overheating of the sensor. Second, due to impedance non-uniformities of the electrolyte material, the accuracy of the sensor temperature measurements may vary. Lastly, measuring the impedance of the electrolyte material can be somewhat complicated requiring higher cost sensor control circuitry.

BRIEF SUMMARY

In a planar oxygen sensor having a pump cell, a reference cell, a sensor chamber and a heating device, a ground plane electrode comprising: a sensing portion having a first sense lead and a second sense lead; and a measuring portion having a first measuring lead and a second measuring lead, wherein the first measuring lead and the second measuring lead have increased surface area relative to said sensing portion such that the resistance between the first measuring lead and the second measuring lead is reduced and wherein the first measuring lead is disposed so as to be communicated with the first sense lead and the second measuring lead is disposed so as to be communicated with the second sense lead.

In a planar oxygen sensor having a pump cell, a reference cell, a sensor chamber, a heating device and a ground plane electrode that includes a sensing portion having a first sense lead and a second sense lead and a measuring portion having a first measuring lead and a second measuring lead, a method for measuring the temperature of the planar oxygen sensor comprising: obtaining a temperature measurement device; communicating the temperature measurement device with the first measuring lead and the second measuring lead; operating the planar oxygen sensor so as to cause the heating device to heat the planar oxygen sensor; and measuring the resistance between the first measuring lead and the second measuring lead.

BRIEF DESCRIPTION OF THE DRAWINGS

The present invention will now be described, by way of an example, with references to the accompanying drawings, wherein like elements are numbered alike in the several figures in which.

DETAILED DESCRIPTION OF AN EXEMPLARY EMBODIMENT

Figure 1:
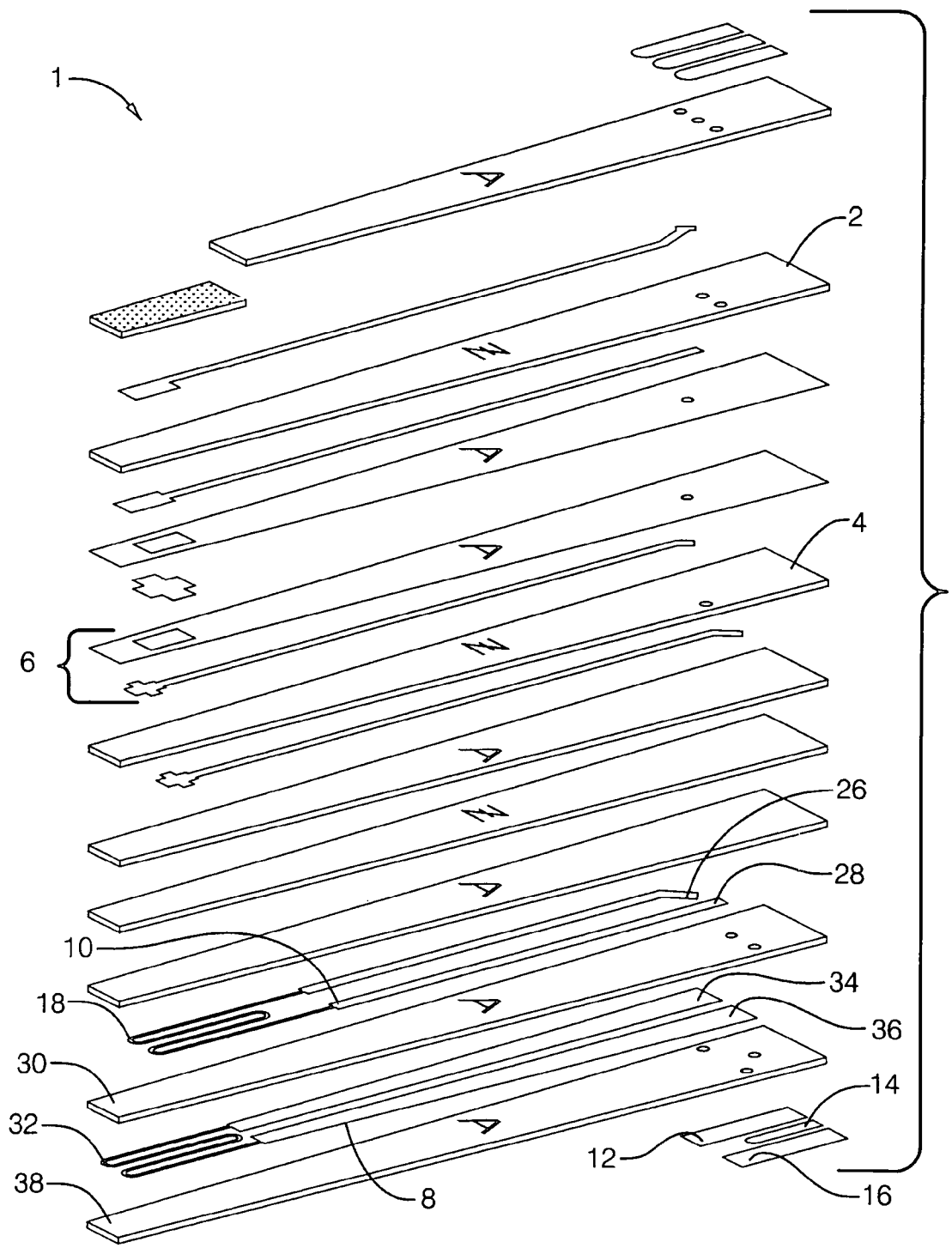
FIG. 1 shows an exploded view of a general planar oxygen sensor in accordance with a first embodiment.
Figure 2:
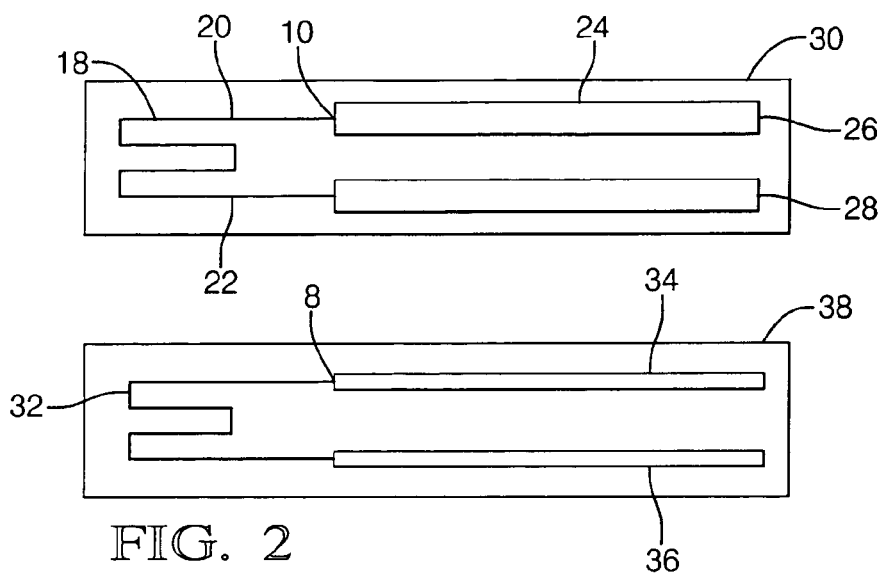
FIG. 2 shows a top down view of a ground plane electrode and a heating device of a planar oxygen sensor in accordance with a first embodiment.
Figure 3:
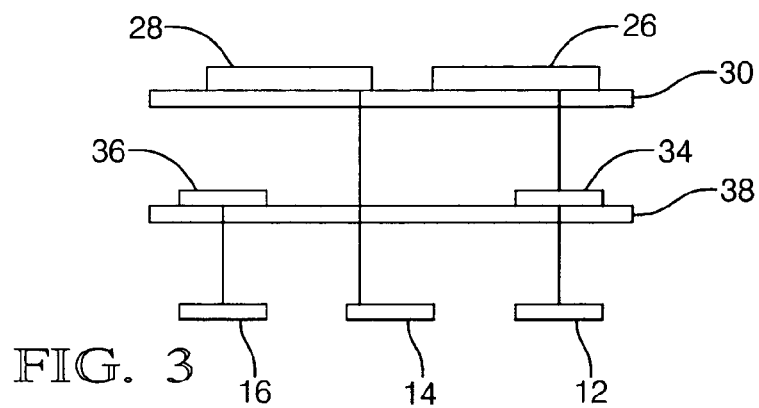
FIG. 3 shows an exploded side view of a planar oxygen sensor in accordance with a first embodiment.

Referring to the drawings, FIG. 1, FIG. 2 and FIG. 3 shows a planar oxygen sensor 1 having a pump cell 2, a reference cell 4, a sensor chamber 6, a heating device 8, a ground plane electrode 10, a ground terminal 12, a resistance measurement terminal 14 and a power terminal 16, in accordance with a first embodiment. Ground plane electrode 10 preferably includes a sensing portion 18 and a measuring portion 24, wherein sensing portion 18 preferably includes a first sense lead 20 and a second sense lead 22 and measuring portion 24 preferably includes a first measuring lead 26 and a second measuring lead 28. Moreover, planar oxygen sensor 1 preferably includes a first isolation layer 30 non-movably associated with ground plane electrode 10 so as to electrically isolate ground plane electrode 10 from heating device 8. In accordance with an exemplary embodiment, first measuring lead 26 is preferably sized relative to second measuring lead 28 such that the resistance between first measuring lead 26 and second measuring lead 28 is reduced (e.g. minimized). In particular, first measuring lead 26 and second measuring lead 28 have increased surface area relative to sensing portion 18.

Also, in accordance with an exemplary embodiment, heating device 8 preferably includes a thermal emitter 32, a first heating device lead 34 and a second heating device lead 36, wherein thermal emitter 32 is communicated with first heating device lead 34 and second heating device lead 36. In addition, planar oxygen sensor 1 preferably includes a second isolation layer 38 non-movably associated with heating device 8 so as to electrically isolate heating device 8 from ground terminal 12, resistance measurement terminal 14 and power terminal 16.

In accordance with a first embodiment, first heating device lead 34 is preferably electrically communicated with first measuring lead 26 and ground terminal 12. Second measuring lead 28 is preferably electrically communicated with resistance measurement terminal 14. Moreover, second heating device lead 36 is preferably electrically communicated with power terminal 16. Also, in accordance with an exemplary embodiment, power terminal 16 and ground terminal 12 are preferably electrically communicated with a power source, such as a power supply or a battery.

Figure 4:
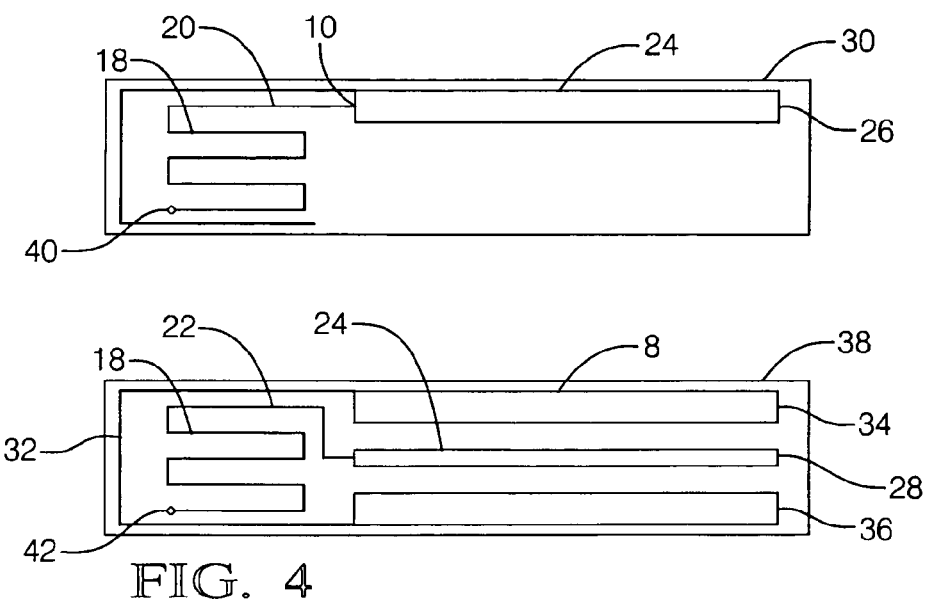
FIG. 4 shows a top down view of a ground plane electrode and a heating device of a planar oxygen sensor in accordance with a second embodiment.
Figure 5:
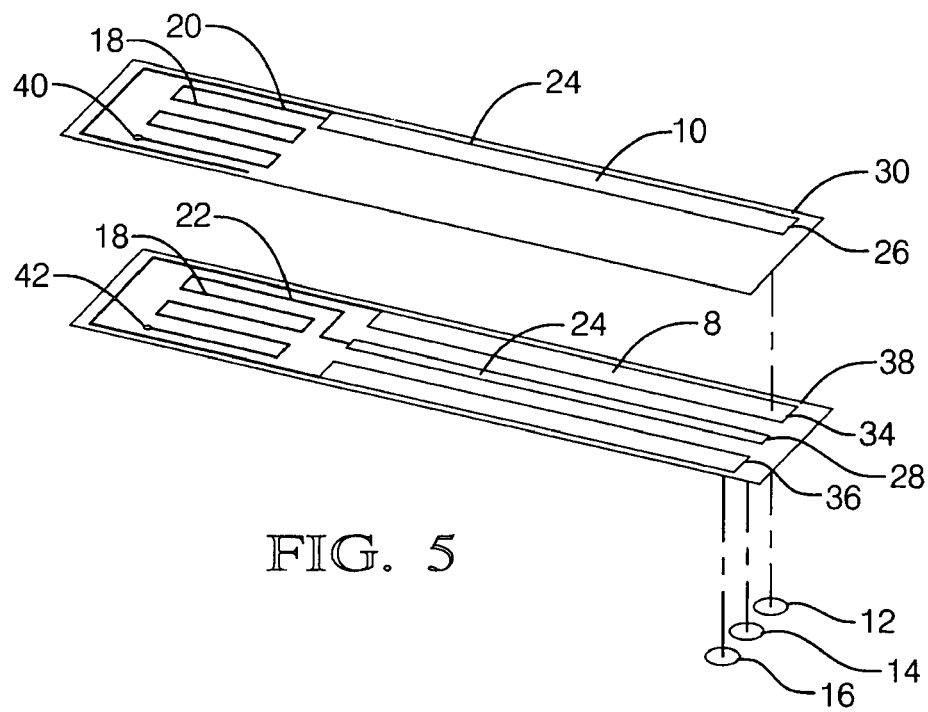
FIG. 5 shows an exploded view of a ground plane electrode and a heating device of a planar oxygen sensor in accordance with a second embodiment.
Figure 7:
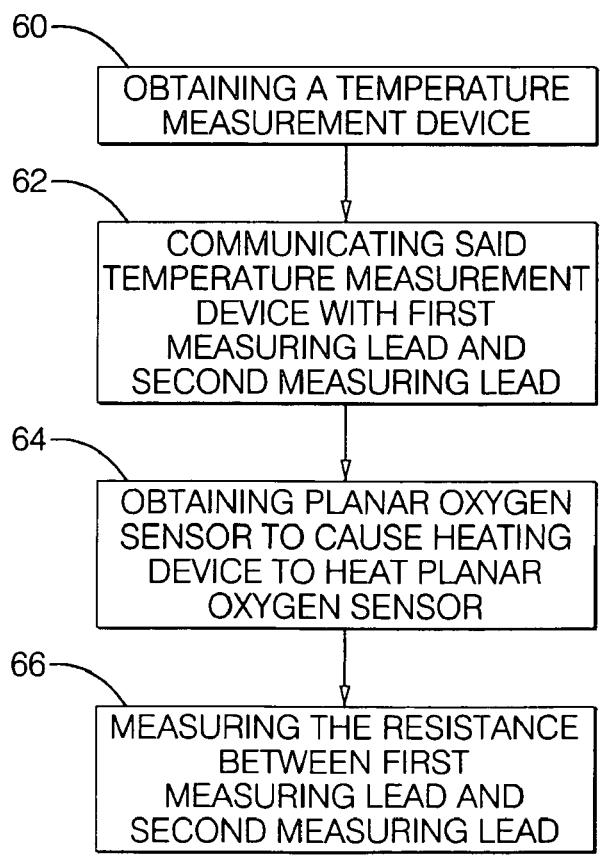
FIG. 7 shows a block diagram describing a method for measuring the temperature of a planar oxygen sensor in accordance with an exemplary embodiment.

Referring to FIG. 4 and FIG. 5, a second embodiment is shown and includes a heating device 8, a ground plane electrode 10, a ground terminal 12, a resistance measurement terminal 14 and a power terminal 16. Heating device 8 preferably includes a thermal emitter 32, a first heating device lead 34 and a second heating device lead 36, wherein thermal emitter 32 is communicated with first heating device lead 34 and second heating device lead 36. Ground plane electrode 10 preferably includes a sensing portion 18 and a measuring portion 24, wherein sensing portion 18 preferably includes a first sense lead 20 and a second sense lead 22 and measuring portion 24 preferably includes a first measuring lead 26 and a second measuring lead 28. Moreover, planar oxygen sensor 1 preferably includes a first isolation layer 30 non-movably associated with first measuring lead 26 and a second isolation layer 38 non-movably associated with second measuring lead 28. In addition, first isolation layer 30 preferably includes a first via 40 and second isolation layer 38 preferably includes a second via 42, wherein the first via 40 and the second via 42 are preferably disposed relative to each other so as to be electrically communicated with each other.

In accordance with a second embodiment, first measuring lead 26 is preferably non-movably associated with first isolation layer 30 and second measuring lead 28 is preferably non-movably associated with second isolation layer 38 so as to allow the combined surface area of first measuring lead 26 and second measuring lead 28 to be increased (e.g. maximized). This keeps the resistance between first measuring lead 26 and second measuring lead 28 to a minimal value.

In accordance with a second embodiment, first heating device lead 34 is preferably electrically communicated with first measuring lead 26 and ground terminal 12. Second measuring lead 28 is preferably electrically communicated with resistance measurement terminal 14. Moreover, second heating device lead 36 is preferably electrically communicated with power terminal 16. Also, in accordance with an exemplary embodiment, power terminal 16 and ground terminal 12 are preferably communicated with a power source, such as a power supply or a battery.

Figure 6:
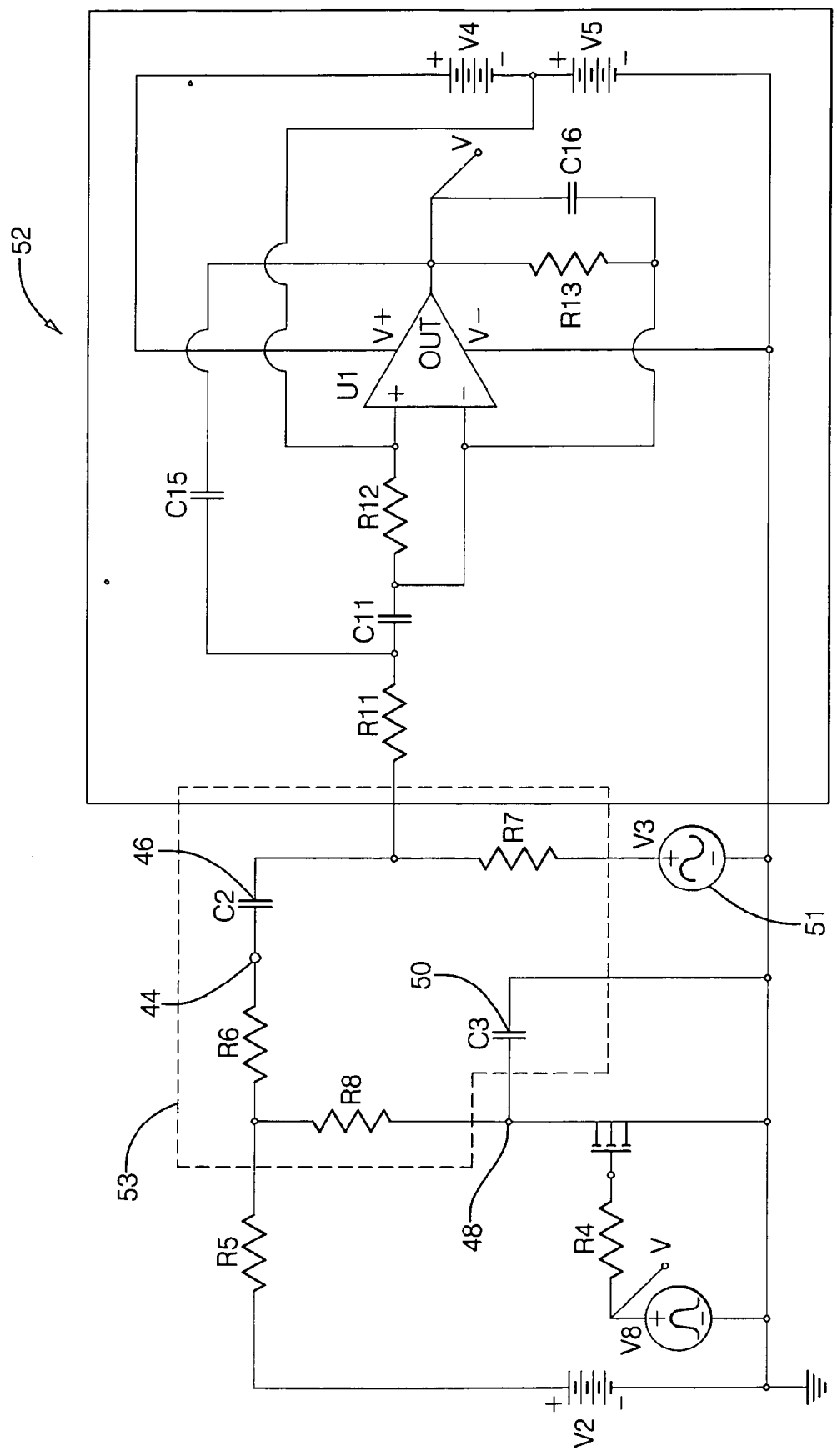
FIG. 6 shows a schematic of a temperature measurement device in accordance with an exemplary embodiment.

Referring to FIG. 6, a schematic of a temperature measurement device 52 is shown and includes a first device terminal 44 communicated with a first capacitor 46 and a second device terminal 48 communicated with a second capacitor 50. Temperature measurement device 52 preferably includes an AC signal source 51 and a voltage divider 53 for introducing an AC signal into planar oxygen sensor 1 and measuring the corresponding voltage drop. In accordance with an exemplary embodiment, AC signal preferably includes an AC signal frequency, wherein the AC signal frequency may be any AC signal frequency suitable to the desired end purpose.

In accordance with an exemplary embodiment, first device terminal 44 is preferably communicated with ground terminal 12 and second device terminal 48 is preferably communicated with resistance measurement terminal 14. In addition, first capacitor 46 and second capacitor 50 are preferably communicated with first device terminal 44 and second device terminal 48, respectively. This preferably allows the AC signal to be introduced into planar oxygen sensor 1 via first device terminal 44 and second device terminal 48 through first capacitor 46 and second capacitor 50, respectively.

Referring to the figures, a method for measuring the temperature of planar oxygen sensor 1 as described hereinabove is illustrated and discussed. In accordance with an exemplary embodiment, a temperature measurement device 52 having a first device terminal 44 and a second device terminal 48 is obtained as shown in step 60. Temperature measurement device 52 is communicated with planar oxygen sensor 1 as shown in step 62. This is preferably accomplished by communicating first device terminal 44 with first measuring lead 26 and by communicating second device terminal 48 with second measuring lead 28. Planar oxygen sensor 1 is then operated so as to cause heating device 8 to heat planar oxygen sensor 1 as shown in step 64. An AC signal is then introduced into planar oxygen sensor 1 via AC signal source 51. The temperature of planar oxygen sensor 1 is then determined by measuring the resistance between the first measuring lead 26 and the second measuring lead 28 using the temperature measurement device 52, as shown in step 66. This is done by measuring the voltage potential difference between first measuring lead 26 and second measuring lead 28 using voltage divider 53.

In accordance with an exemplary embodiment, this voltage potential difference is then converted into a resistance value responsive to the resistance between first measuring lead 26 and second measuring lead 28, wherein the resistance is then converted into a temperature value, responsive to the temperature of planar oxygen sensor 1, by temperature measuring device 52. In accordance with an exemplary embodiment, the relationship of the resistance between first measuring lead 26 and second measuring lead 28 and the temperature of the planar oxygen sensor 1 is preferably responsive to the material used to construct sensing portion 18 and/or measuring portion 24.

In accordance with an exemplary embodiment, temperature measurement device 52 may be any measuring device suitable to the desired end purpose. Also in accordance with an exemplary embodiment, voltage divider 53 may be any voltage divider circuitry, device and/or method suitable to the desired end purpose. Moreover, in accordance with an exemplary embodiment, AC signal source 51 may be any AC signal source, circuitry or device suitable to the desired end purpose.

In accordance with an exemplary embodiment, sensing portion 18 of ground plane electrode 10 is preferably constructed of either a negative resistance temperature detector material or a positive resistance temperature detector material. However, sensing portion 18 may be constructed of any material suitable to the desired end purpose.

In accordance with an exemplary embodiment, measuring portion 24 of ground plane electrode 10 is preferably constructed of a precious metal such as platinum or a composite of gold, rhodium and platinum. However, measuring portion 24 may be constructed of any material suitable to the desired end purpose.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A planar oxygen sensor comprising
a gas sensing arrangement comprising a pump cell, a reference cell spaced apart from the ground cell, and a sensor chamber disposed between the pump cell and the ground cell,
a heating device proximate to the gas sensing arrangement for heating the gas sensing arrangement to an operating temperature, said heating device comprising a first heating device lead and a second heating device lead, said second heating device lead being adapted to be connected to a power terminal of a power source,
a ground plane electrode adapted for temperature measurement and comprising a first lead, a second lead, and a temperature sensing portion electrically interconnecting the first lead and the second lead, said temperature sensing portion having an electrical resistance indicative of temperature, wherein at least said first lead is disposed between the gas sensing arrangement and the heating device and is electrically connected to said first heating device lead, said first lead having a surface area greater than the temperature sensing portion and an electrical resistance less than the electrical resistance of the temperature sensing portion,
an isolation layer disposed between the ground plane electrode and the heating device;
a ground terminal connected to the first lead and the first heating device lead,
a resistance measurement terminal connected to the second lead, and
a power terminal connected to the second heating device lead,
whereby the ground terminal and the resistance measurement terminal are adapted to be connected to an electrical circuit for measuring the electrical resistance therebetween, said electrical resistance being indicative of temperature, and
whereby said power terminal and said ground terminal are adapted to be connected to a power source for providing electrical current to the heating device.

2. A planar oxygen sensor according to claim 1 further comprising a temperature measurement device comprising an electrical circuit connected to the ground terminal and the resistance measurement terminal.

3. A planar oxygen sensor according to claim 2 wherein the temperature measurement device includes a first capacitor connected to the ground terminal and a second capacitor connected to the resistance measurement terminal.

4. A planar oxygen sensor according to claim 2 wherein the temperature measurement device includes an AC signal source.

* * * * *